United States Patent [19]
Ferlic

[11] Patent Number: 6,021,175
[45] Date of Patent: Feb. 1, 2000

[54] X-RAY FILTER

[76] Inventor: Daniel J. Ferlic, 406 Birchwood Ave., White Bear Lake, Minn. 55110

[21] Appl. No.: 09/048,726

[22] Filed: Mar. 26, 1998

[51] Int. Cl.[7] .................................................... G21K 3/00
[52] U.S. Cl. ......................... 378/159; 378/156; 378/158
[58] Field of Search .................................. 378/159, 156, 378/158

[56] References Cited

U.S. PATENT DOCUMENTS 4,288,695  9/1981  Walters et al. ...................... 250/455 T

*Primary Examiner*—David P. Porta
*Assistant Examiner*—Michael J. Schwartz
*Attorney, Agent, or Firm*—Kinney & Lange P.A.

[57] ABSTRACT

An x-ray filter is used to permit higher intensity x-ray exposure to the upper thoracic spine while maintaining a normal level of x-ray exposure to the cervical spine. The resulting x-ray image allows a viewer to count the seven cervical vertebrae in order to identify the position of the first and second thoracic vertebrae. The filter is formed by a pair or mating blocks of x-ray absorbing material. The filter has a first region for absorbing x-ray radiation to decrease exposure of the cervical spine and has a second region with a V-shaped opening which allows higher x-ray transmission to the thoracic spine while reducing exposure on areas adjacent to the thoracic spine. The filter is formed by two shaped filter blocks which fit together to create the first and second regions. The edges of the filter blocks which form the V-shaped opening are beveled to create a generally trapezoidal exposure region which is aligned with the upper thoracic spine. A similar x-ray filter for use in a lateral view of the hip reduces exposure to areas commonly overexposed adjacent to the head and neck of the femur in a lateral projection.

20 Claims, 9 Drawing Sheets

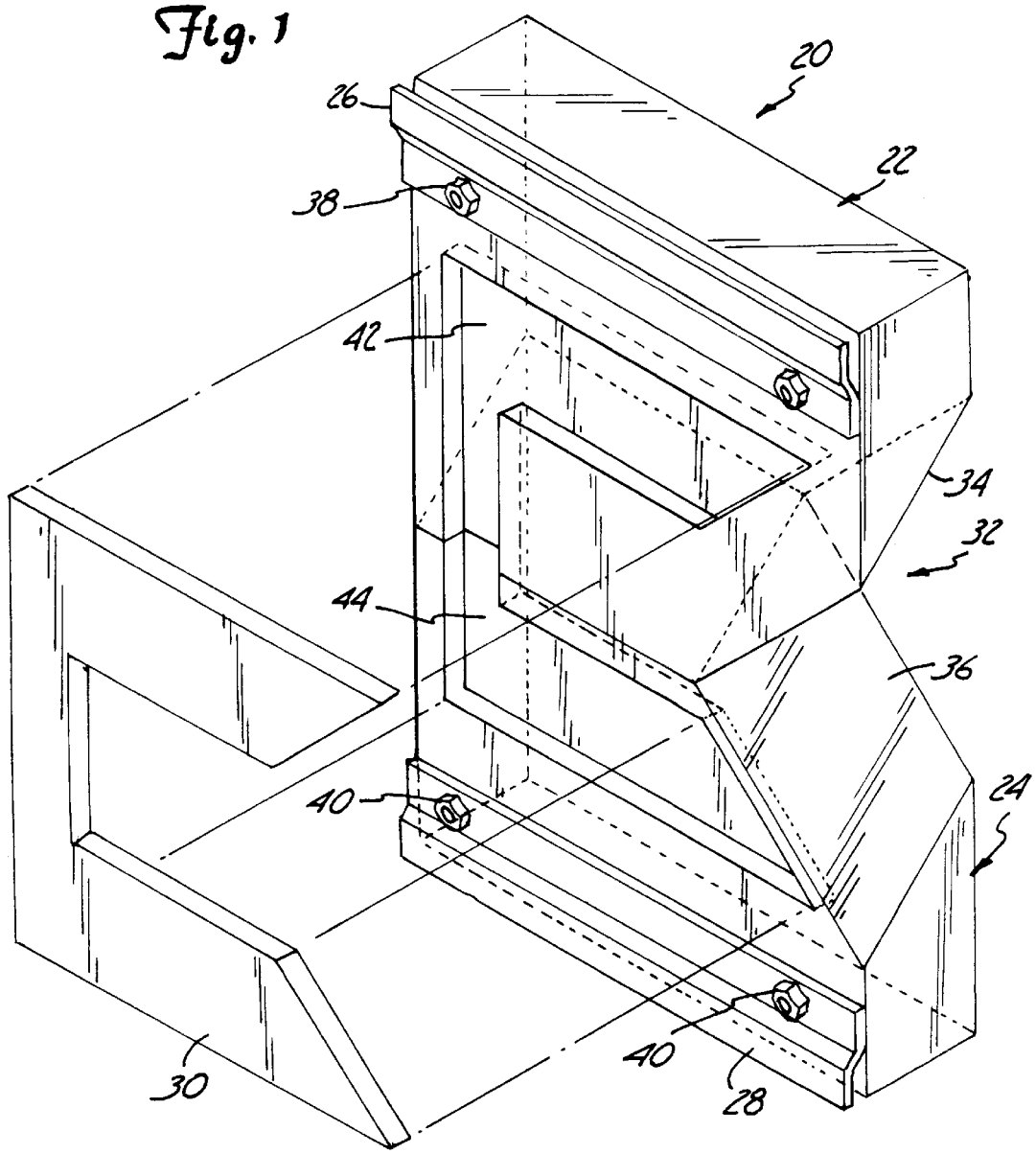

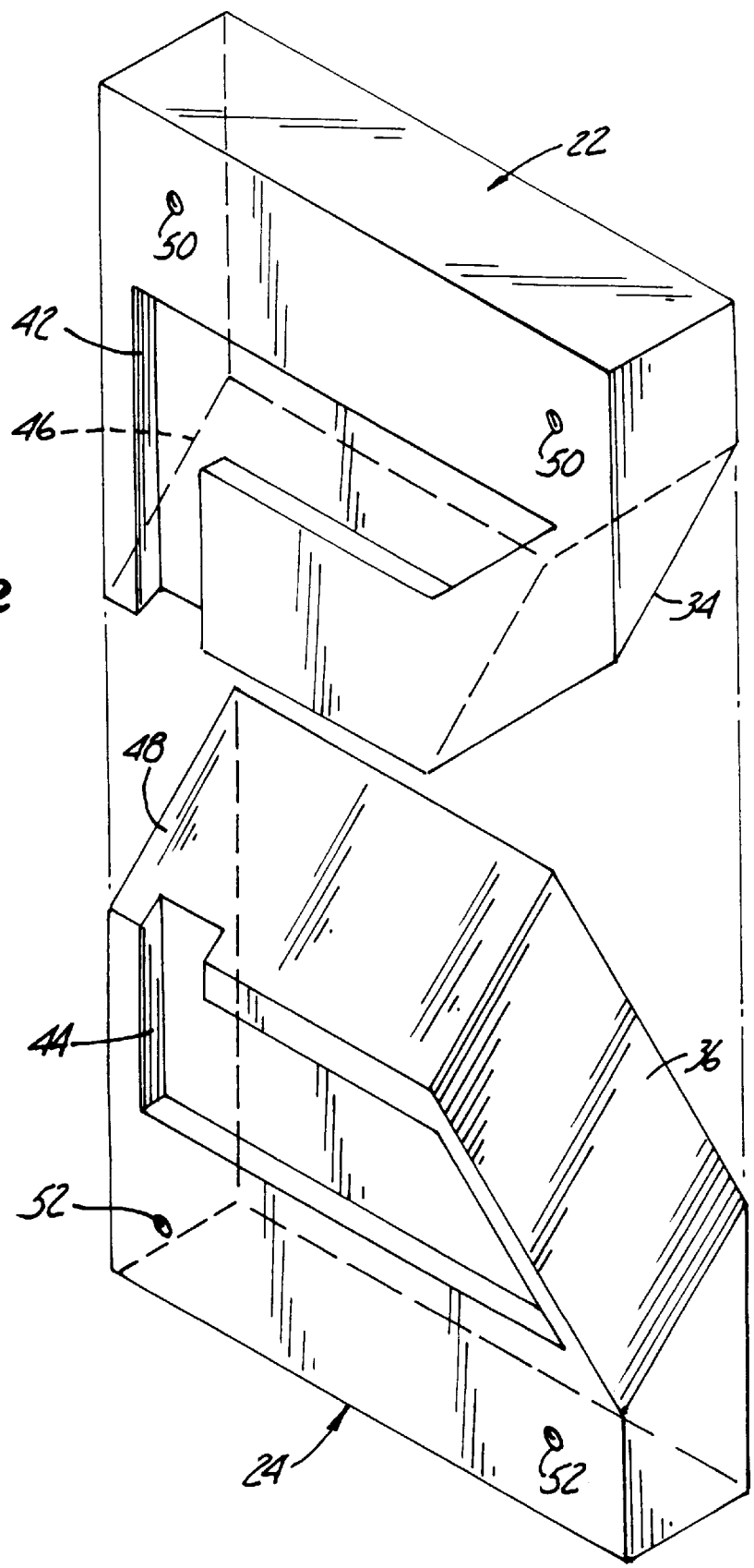

X-RAY FILTER

BACKGROUND OF THE INVENTION

The present invention relates to a filter for use with x-ray examining devices. In particular, the invention is a filter which is used to improve the quality of x-ray images of the cervical-thoracic region of the spine in a lateral projection.

X-ray imaging is an important diagnostic tool which is used by medical professionals on a daily basis. An x-ray system has several fundamental components: a source of an ionizing or penetrative radiation (normally an x-ray tube), and object plane in which the object (typically a patient) is positioned, an image plane on the opposite side of the object plane from the radiation source, and an image recording medium or device disposed at the image plane. The image recording medium may be an x-ray sensitive film, a fluorescent display screen, or an electronic image amplifier.

One of the many uses of x-ray examination is in an emergency room to determine the nature and extent of trauma in accident cases. For example, a patient may be wheeled into the emergency room with a neck collar which has been applied because of a suspected cervical injury. The cervical/thoracic region of the spine should be properly visualized before moving the patient. In the past, the images of the cervical/thoracic region have been of poor quality because of the difference in thickness and mass of the cervical and thoracic regions.

In order to obtain a proper exposure of the thoracic spine, a relatively high level of x-ray exposure (similar to a lateral lumbar spine exposure) is required because in the lateral projection the thoracic spine has both high tissue and bone density. This high level of exposure greatly exceeds the exposure levels needed to image the cervical spine. As a result, an x-ray image of the cervical/thoracic region will either show the thoracic spine region while the cervical spine region is significantly overexposed, or show the cervical spine region with the thoracic spine region significantly underexposed.

Typically, a physician examining x-ray images of a patient with suspected cervical injury will attempt to count the cervical vertebrae in order to locate the seventh cervical vertebra and the first thoracic vertebra. It is important to determine whether the seventh cervical and first thoracic vertebrae are aligned before moving a patient in order to avoid causing permanent spinal cord injuries.

There is a need for a improved x-ray system in which the cervical and upper thoracic spine regions can be imaged in a single x-ray image with acceptable levels of x-ray exposure in both the cervical and thoracic spine regions.

SUMMARY OF THE INVENTION

This invention involves a filter for use in medical x-ray apparatus. The filter allows a relatively high intensity x-ray exposure in the upper thoracic spine of the patient, while allowing a normal level of exposure to the cervical spine. This density compensation allows the viewer to count the seven cervical vertebrae to identify the position of the first and second thoracic vertebrae. The filter comprises a body of radiation absorbing material having a shaped opening to transmit more radiation to the upper thoracic spine relative to the absorbing material transmitting reduced radiation to the cervical spine.

BRIEF DESCRIPTION OF THE DRAWINGS

FIG. 1 is a perspective view, partially exploded, showing the x-ray filter of the present invention.

FIG. 2 is an exploded perspective view of the filter blocks of the x-ray filter of FIG. 1.

DETAILED DESCRIPTION OF THE PREFERRED EMBODIMENTS

Figure 6:
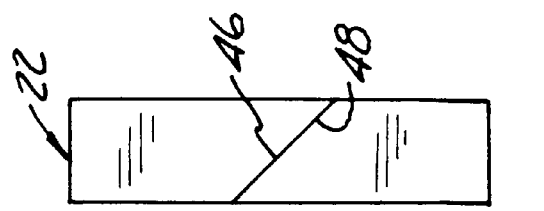
FIG. 6 is a left end view of the filter blocks.
Figure 5:
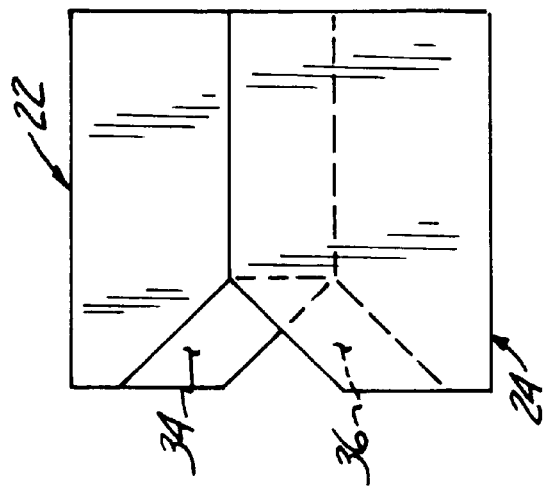
FIG. 5 is a rear view of the filter blocks.
Figure 4:
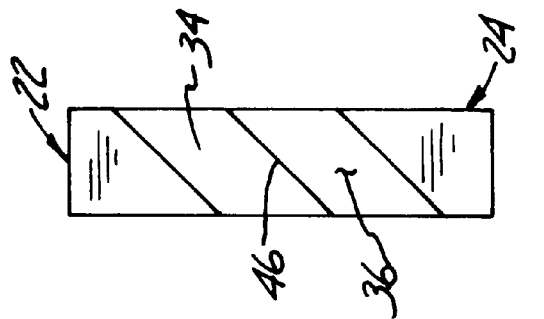
FIG. 4 is a right end view of the filter blocks.
Figure 3:
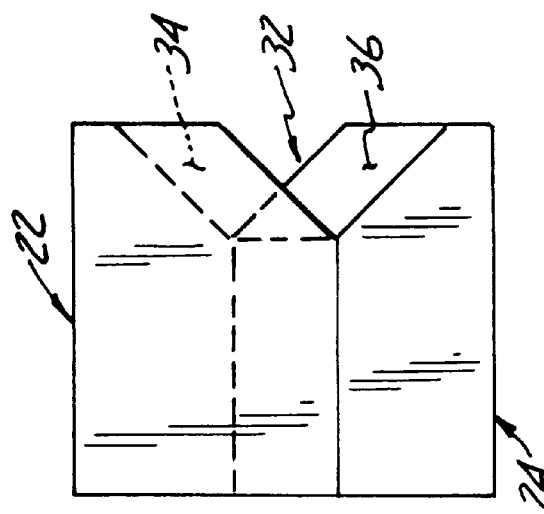
FIG. 3 is a front view of the filter blocks.

In FIG. 1, an x-ray filter of the present invention is shown in a partially exploded perspective view. Filter 20 includes upper filter block 22, lower filter block 24, upper guide rail 26, lower guide rail 28, and lead tap 30.

X-ray filter 20 is used to filter the beam of x-rays produced by an x-ray source so that both the cervical spine and the upper thoracic spine can be properly exposed in a single x-ray image. Filter 20 must significantly reduce the level of x-ray exposure of the cervical spine 400 percent or more, because a very high level of x-ray exposure (equal to a lateral lumbar spine) is required in the area of the lateral upper thoracic spine. In the prior art, it is not unusual to expose the cervical spine 400 percent or more than necessary.

Filter blocks 22 and 24 are shaped to fit together, so that they form a first region which absorbs x-ray radiation to a level which allows proper exposure of the cervical spine. In the orientation found in FIG. 1, the left side of filter 20 is oriented toward a patient's head, and the right side is oriented toward the patient's feet. The left half of filter 20 forms a first region which is aligned with the cervical spine, while the right half of filter 20 is aligned with the upper thoracic spine of the patient. Within the right half of filter 20 is triangular opening 32, which is formed by beveled surface 34 of upper block 22 and beveled surface 36 of lower block 20.

Filter blocks 22 and 24 are made of a material capable of absorbing x-ray radiation. The thickness of the radiation absorbing material must absorb at least 80 percent of the radiation for the kvp (kilovolt peak) used for the swimmer's view of the lateral cervical-thoracic spine. This range is generally from about 80 to about 130 kvp. The radiation absorbing material may consist of a single material or a composite material. Suitable radiation absorbing materials include aluminum, copper, tin, lead and gold, as well as polymeric material filled with radiation absorbing materials. Multiple layered materials such as aluminum with copper cladding, or layers of aluminum, copper and tin are suitable.

In a preferred embodiment, filter blocks 22 are aluminum with a thickness of about 15 mm to 35 mm, although larger dimensions, depending upon radiation absorbing properties, may be useful. When the x-ray filter of the present invention is used with computed or radiography, the contrast enhancement provided by those techniques can cause the edges of the filter to be visible. In order to reduce this artifact to do an acceptable visual level, a beryllium/aluminum filter material, rather than all aluminum. This would decrease the x-ray density of aluminum/beryllium for a given thickness effecting a reduction in edge visibility for the same thickness as an all aluminum filter.

Rail 26 is attached to upper block 22 by screws 38. Lower rail 28 is attached to lower filter block 24 by screws 40. Together, upper rail 26 and lower rail 28 allow filter 20 to be mounted in a filter holder (not shown) within the x-ray apparatus.

In order to further limit the exposure of x-rays to the cervical and upper thoracic region, lead tap 30 is mounted within grooves 42 and 44 in the front or back surface of filter blocks 22 and 24, respectively.

In use, filter 20 is positioned between the source of the x-ray beam and the object plane where the patient is positioned. Opening 32 is generally aligned with the shoulder of the patient so that more radiation is transmitted to the upper thoracic spine relative to the cervical spine. As a result, a high intensity x-ray exposure of the upper thoracic spine is permitted, while a normal level of exposure to the cervical spine is provided. In addition, the triangular opening extends into the upper thoracic region reducing the exposure on both sides of the thoracic spine and as a result producing less scatter radiation thereby increasing contrast in the image. This density compensation provided by filter 20 allows the viewer to count the seven cervical vertebrae to identify the position of the first and second thoracic vertebrae.

FIG. 2 is an exploded view showing upper filter body 22 and lower filter body 24. Filter bodies 22 and 24 are separated to show beveled surfaces 46 and 48, which mate together when blocks 22 and 24 are joined to form filter 20.

Beveled surface 46 is preferably oriented at 45 degrees (plus or minus 10 degrees) to the front surface of filter block 22. Beveled surface 48 is oriented at 135 degrees (plus or minus 10 degrees) of the front surface of filter block 24. As a result, when filter blocks 22 and 24 are brought together (as in FIG. 1) surfaces 46 and 48 mate with one another. The beveled orientation of surfaces 46 and 48 minimize visualization of surfaces 46 and 48 on the x-ray film.

In addition, changing the beveled angle on the beveled surface 34 and 36, rounding the edges of the beveled surfaces 34 and 36 which are greater than 90 degrees, and narrowing to a thin edge those edges which are less than 90 degrees also will reduce visibility of edges when the filter is used with computed or digital radiography.

As shown in FIG. 2, upper block 22 has a pair of threaded mounting holes 50 for receiving mounting screws 38 (FIG. 1). Similarly, lower block 24 has a pair of mounting holes 52 for receiving mounting screws 40.

FIGS. 3–6 show front, right (or foot) end, rear and left (or head) end views of blocks 22 and 24. For simplicity, grooves 42 and 44 are not shown in FIGS. 3–6.

Figure 7:
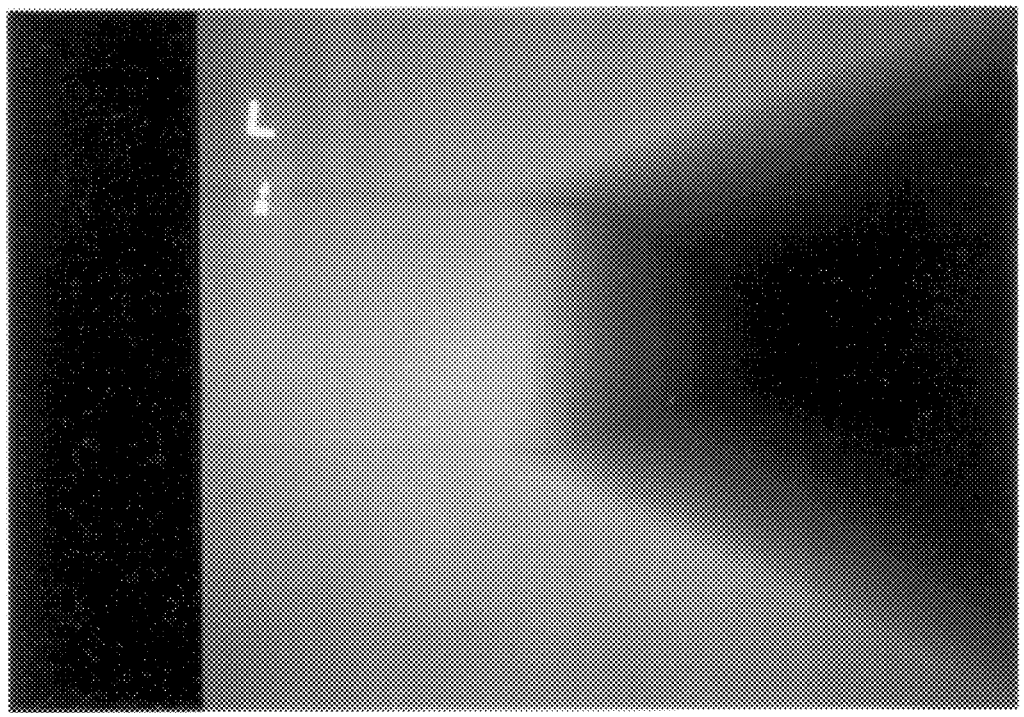
FIG. 7 is a photograph showing a trapezoidal exposure pattern produced by the x-ray filter of the present invention.

FIGS. 3–6 illustrate how beveled edges 46 and 48 mate, and how oppositely beveled surfaces 34 and 36 define opening 32. The beveling of the edges which define opening 32, provides a gradation in density which avoid prominent edges from being viewed on the x-ray film. The opposite bevels of surfaces 34 and 36 create, in effect, a trapezoidal shaped area of greater exposure. This trapezoidal region is illustrated in the photograph shown in FIG. 7. The darker trapezoidal region illustrates a higher level of exposure.

Figure 8:
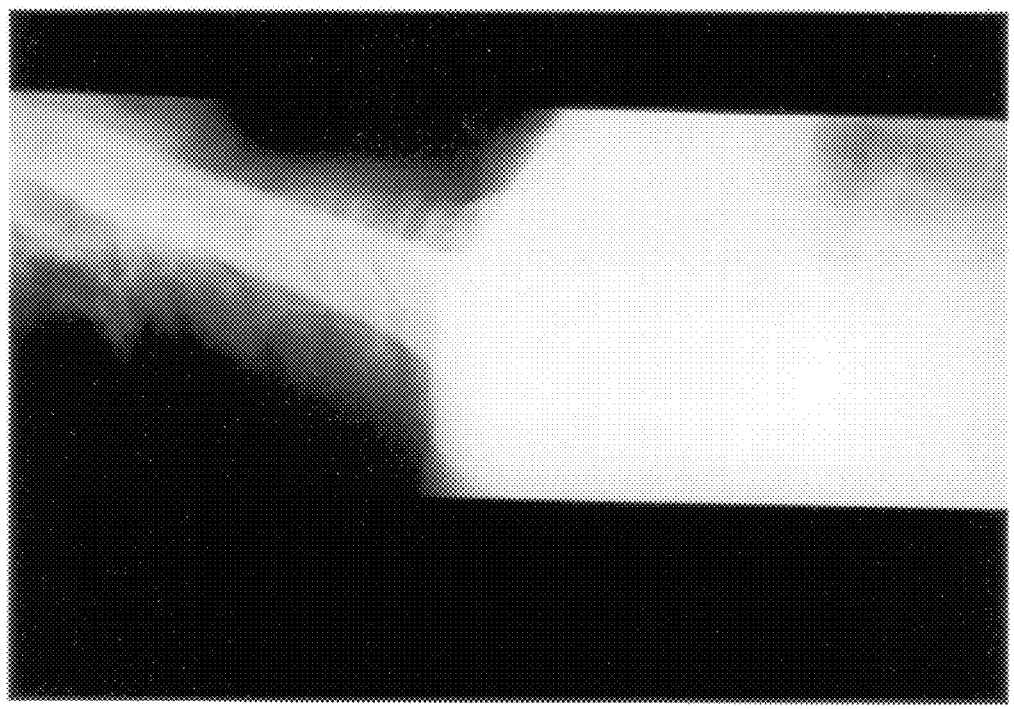
FIG. 8 is an x-ray image of a cervical/thoracic spine region of a patient produced without the filter of the present invention and with an exposure which allows the cervical vertebrae to be visible but underexposes the upper thoracic spine.
Figure 9:
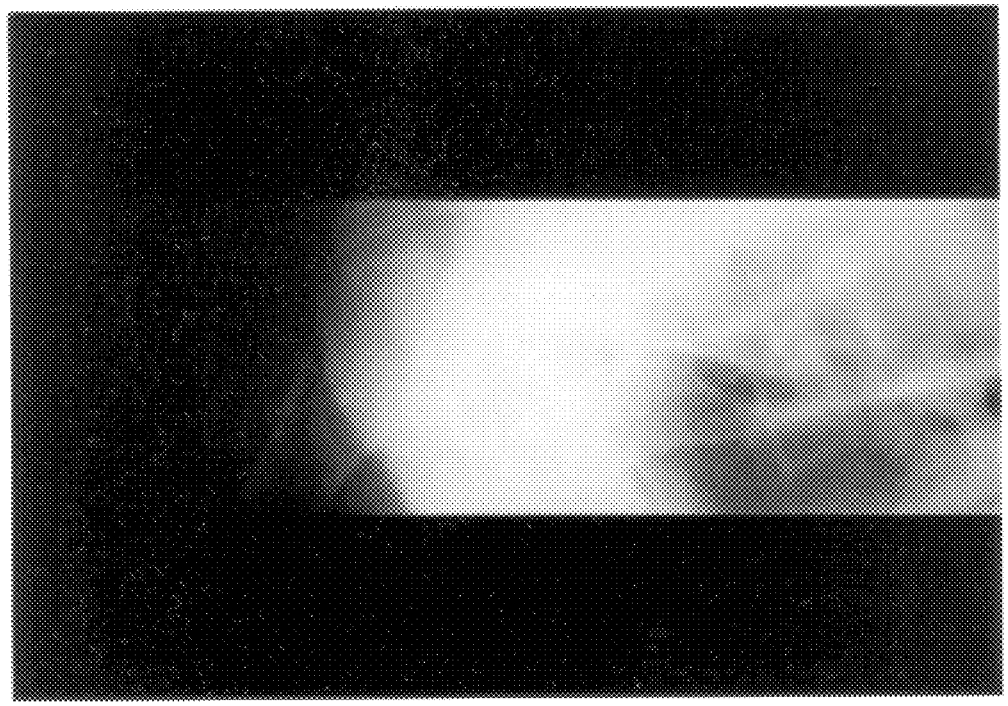
FIG. 9 is an x-ray image of a cervical/thoracic spine region of a patient produced without the filter of the present invention and in which portions of the upper thoracic spine are visible, however the cervical spine is overexposed.
Figure 10:
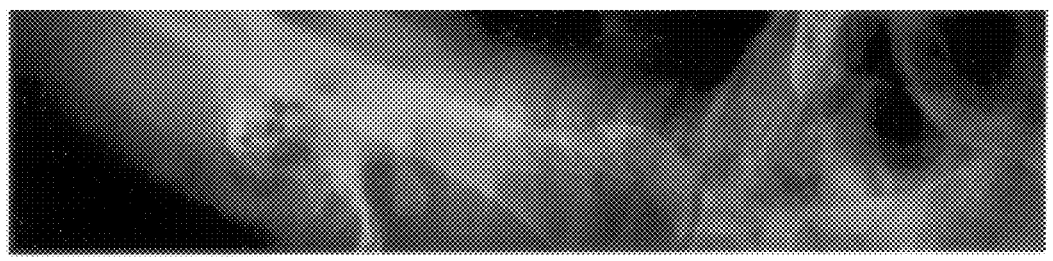
FIG. 10 is an x-ray image of a cervical/thoracic spine region of a patient produced using the x-ray filter of the present invention, in which both cervical and thoracic vertebrae are visible because the filter equalizes the different thickness between the cervical spine and the thoracic spine in the lateral projection.

FIGS. 8–10 are a series of photographs which illustrate the effectiveness of x-ray filter 20 in allowing high quality, usable x-ray images of the cervical and upper thoracic spine.

In each of the photographs shown in FIGS. 8–10, the x-ray image is of a lateral view of the cervical/thoracic spine. The photographs are oriented horizontally, with the patients head at the left end and the patients chest at the right end. In each case, the patient was placed in a "swimmers" pose in which the patients arm closest to the image claim was raised over the patient's head.

FIG. 8 is a image taken without the x-ray filter of the present invention. The x-ray exposure level was set to expose the cervical spine and upper thoracic spine. In this image, a number of the cervical vertebrae are visible (as is the patient's raised arm). The upper thoracic spine region, however, is badly underexposed, and it is not possible to locate the junction of the seventh cervical vertebra and the first thoracic vertebra.

FIG. 9 is a similar x-ray image taken in which exposure levels were set to allow viewing of the upper thoracic spine region. The cervical spine region is at the left end of the photograph, and is so overexposed that it is entirely dark and unusuable.

FIG. 10 is an x-ray image produced using the x-ray filter of the present invention. In FIG. 10, the cervical and upper thoracic spine regions are properly exposed. An image like the one shown in FIG. 10 allows the attending physician to locate the junction of the seven cervical vertebra and first thoracic vertebra and to determine whether they are properly aligned.

Figure 11:
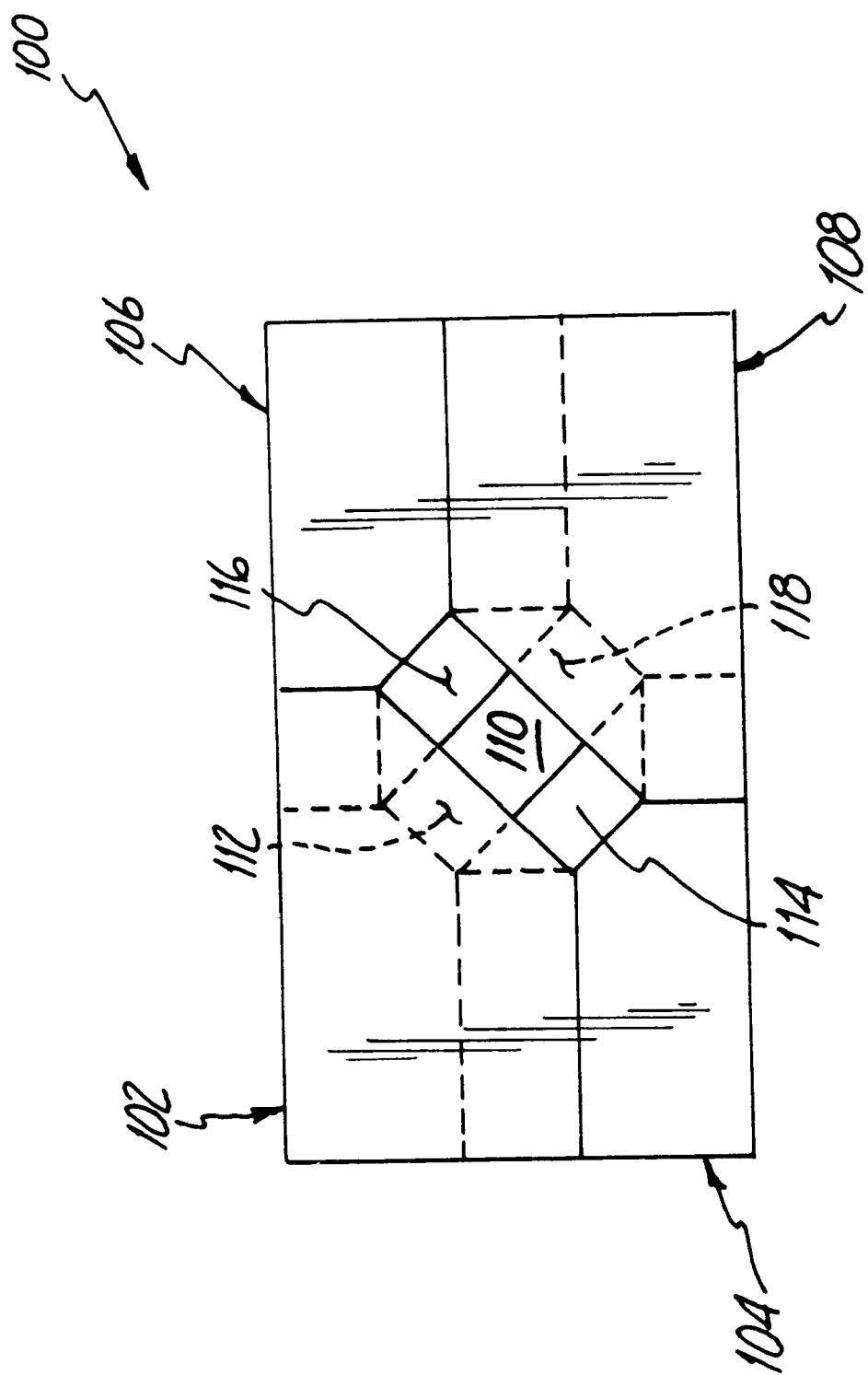
FIG. 11 is another embodiment of the present invention in which the filter is formed by four filter blocks, in an arrangement for a hip filter.
Figure 12:
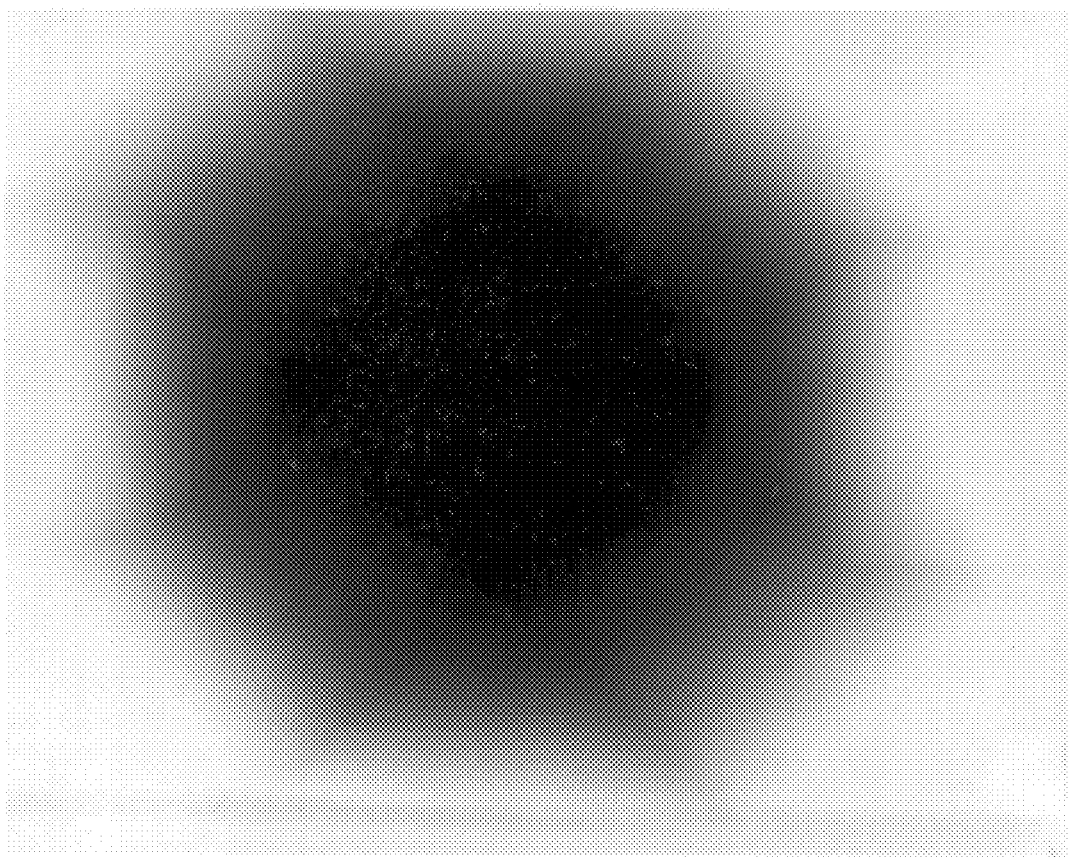
FIG. 12 is an x-ray image showing an octagonal exposure pattern generated with the filter of FIG. 11.

FIG. 11 is a front view of filter 100, which is another embodiment of the present invention. Filter 100 includes 4 filter blocks, 102, 104, 106, and 108 which are joined together and which have a central opening 110 which permits greater x-ray exposure. As in filter 20 of FIG. 1, x-ray filter 100 has beveled surfaces surrounding opening 110. Each of the beveled surfaces 112, 114, 116 and 118 is oppositely beveled to its adjacent neighboring beveled surfaces. Bevel angles are preferably 25 degrees (plus or minus 10 degrees) and the thickness of filter 100 is preferably about 25 mm (about one inch). The net result is an octagonal (or nearly circular) pattern of higher x-ray transmission, as illustrated in FIG. 12. Filter 110 can be used in a variety of applications where a particular region requires a higher level of x-ray exposure than neighboring regions, but it is important to be able to view the neighboring region in the same x-ray image. Such a region, for example, would be a lateral view of the hip. The design of this filter reduces the scatter radiation by reducing exposure to areas commonly overexposed adjacent to the head and neck of the femur in a later projection.

Although the present invention has been described with reference to preferred embodiments, workers skilled in the art will recognize that changes may be made in form and detail without departing from the spirit and scope of the invention.

I claim:

1. An x-ray filter comprising x-ray radiation absorbing material having a first region for absorbing x-ray radiation to decrease exposure of the cervical spine and a second region shaped opening therein which allows higher x-ray transmission therethrough in the upper thoracic spine area of the body of a patient than in the cervical spine area of the body of the patient, the edges of said radiation absorbing material disposed between the faces of the radiation absorbing material and delineating the shaped opening being beveled.

2. The x-ray filter of claim 1 wherein the opening is generally triangular.

3. The x-ray filter of claim 2 wherein the beveled edges are oppositely oriented to define a first inclined surface adjacent the opening and facing forward and a second inclined surface adjacent the opening of facing rearward.

4. The x-ray filter of claim 3 and further comprising a lead tap attached to the first region.

5. The x-ray filter of claim 1 wherein the absorbing material contains aluminum.

6. The x-ray filter of claim 1 wherein the filter has a thickness of at least about 15 to 30 mm.

7. The x-ray filter of claim 1 wherein the shaped opening creates a generally trapezoidal pattern of higher x-ray transmission.

8. An x-ray filter comprising first and second filter blocks of x-ray radiation absorbing material which are positioned adjacent one another to form a first radiation absorbing region and a second region having a shaped opening which allows higher x-ray transmission than the first region, the shaped opening being defined by a first beveled surface of the first filter block and a second beveled surface of the second filter block, the first beveled surface facing toward a front of the x-ray filter and the second beveled surface facing toward a rear of the x-ray filter.

9. The x-ray filter of claim 8 and further comprising third and fourth filter blocks adjacent the first and second filter blocks, the first, second, third and fourth filter blocks together defining the opening in a central portion of the x-ray filter.

10. The x-ray filter of claim 9 wherein the third filter block has a third beveled surface which faces toward the rear of the x-ray filter and the fourth filter block has a fourth beveled surface which faces toward the front of the x-ray filter.

11. The x-ray filter of claim 9 wherein the opening produces a generally octagonal pattern of higher x-ray transmission.

12. The x-ray filter of claim 8 wherein the opening is generally triangular.

13. The x-ray filter of claim 8 wherein the opening produces a generally trapezoidal pattern of higher x-ray transmission.

14. The x-ray filter of claim 8 wherein the first and second filter blocks have a thickness of greater than about 15 mm.

15. An x-ray filter comprising x-ray radiation absorbing material comprising a plurality of x-ray radiation absorbing members having oppositely beveled surfaces which define a triangular shaped opening which allows higher x-ray transmission in a generally trapezoidal shaped exposure pattern.

16. An x-ray filter comprising x-ray radiation absorbing material having a first region for absorbing x-ray radiation to decrease exposure and a second region shaped opening therein which allows higher x-ray transmission therethrough in a hip region of the body of a patient than in areas of the body of the patient adjacent to a head an neck of a femur in the hip region, the edges of said radiation absorbing material disposed between the faces of the radiation absorbing material and delineating the shaped opening being beveled.

17. The x-ray filter of claim 16 wherein the opening is generally diamond-shaped.

18. The x-ray filter of claim 17 wherein the beveled edges are oppositely oriented to define first inclined surfaces adjacent the opening and facing forward and second inclined surfaces adjacent the opening of facing rearward.

19. The x-ray filter of claim 16 wherein the absorbing material contains aluminum.

20. The x-ray filter of claim 16 wherein the shaped opening creates a generally octagonal pattern of higher x-ray transmission.

* * * * *